(12) United States Patent
Wu et al.

(10) Patent No.: US 8,464,586 B2
(45) Date of Patent: Jun. 18, 2013

(54) VIBRATION WAVE OUTPUT INSTRUMENT AND METHOD OF USING THE SAME

(75) Inventors: Yu-Min Wu, Sanxia Township (TW); Chin-Wen Yang, Taoyuan (TW); Chih-Hsiung Yu, Taoyuan (TW); Hsiao-Cheng Lin, Hsinchu (TW); Hsin-Hsueh Wu, Kaohsiung (TW)

(73) Assignee: Quanta Computer Inc., Taoyuan Shien (TW)

( * ) Notice: Subject to any disclaimer, the term of this patent is extended or adjusted under 35 U.S.C. 154(b) by 621 days.

(21) Appl. No.: 12/659,552

(22) Filed: Mar. 12, 2010

(65) Prior Publication Data

US 2011/0083510 A1    Apr. 14, 2011

(30) Foreign Application Priority Data

Oct. 8, 2009    (TW) .............................. 98134161 A (51) Int. Cl.
*G01N 29/04* (2006.01)
(52) U.S. Cl.
USPC ........................................... 73/584

(58) Field of Classification Search
USPC ........................................... 73/584
See application file for complete search history.

(56) References Cited

U.S. PATENT DOCUMENTS

| | | | |
|---|---|---|---|
| 3,477,422 A | 11/1969 | Jurist, Jr. et al. | |
| 3,575,368 A * | 4/1971 | Thomas et al. | 248/572 |
| 5,944,665 A | 8/1999 | Iino et al. | |
| 6,932,738 B2 * | 8/2005 | Aoki et al. | 477/5 |
| 8,277,382 B2 * | 10/2012 | Matsumura et al. | 600/459 |
| 2004/0122324 A1 * | 6/2004 | Zan | 600/459 |

FOREIGN PATENT DOCUMENTS

| CN | 1846632 A | 10/2006 |
|---|---|---|
| CN | 101203182 A | 6/2008 |

* cited by examiner

*Primary Examiner* — Hezron E Williams
*Assistant Examiner* — Mark A Shabman
(74) *Attorney, Agent, or Firm* — Rabin & Berdo, P.C.

(57) ABSTRACT

A vibration wave output instrument and its use method are provided. The vibration wave output instrument has a base, a vibration device, a pressure device, and a position mechanism. The position mechanism brings both the vibration device and the pressure device to a target region. The pressure device pushes the vibration device to touch against the target region. The vibration device outputs vibration waves beneath the target region.

11 Claims, 6 Drawing Sheets

VIBRATION WAVE OUTPUT INSTRUMENT AND METHOD OF USING THE SAME

RELATED APPLICATIONS

This application claims priority to Taiwan Application Serial Number 98134161, filed Oct. 8, 2009, which is herein incorporated by reference.

BACKGROUND

1. Technical Field

The disclosure relates to a signal output device, more particularly to a vibration wave output instrument and a method of using the same.

2. Description of Related Art

When elderly people suffer from Osteoporosis or Osteoarthritis syndrome, ache that occurs from Osteoporosis or Osteoarthritis syndrome tortures the elderly people a lot. In order to get information of people's human bone mineral density, and to diagnose the condition of people's hip joint (e.g. slack or loose), one of the methods is to send some vibration waves into a human body from a signal output source of a vibration tool (vibrator) through a target region (e.g. limbs) of the human body. When the vibration waves move in the human body and hit the tested bones, some reflective waves will be generated from the tested bones to move outwards from the human body. Then, the reflective waves will be collected and analyzed to figure out the information of human bone mineral density and the health condition of the hip joint, so as to further evaluate the health condition of the tested bones and determine a proper medical treatment according to the collected information.

However, because the skin surfaces of the target region are irregularly unplaned, and the vibration tool is provided with a certain weight, an operator is hard to stably handle and position the vibration tool at the target region precisely if the vibration tool is provided without an effective and easy means for tightly fixing the vibration tool on the target region thereof. Therefore, a deviated reflective wave other than the actual one may be collected to further affect the test result.

SUMMARY

Therefore, an aspect of the present disclosure is to present a vibration wave output instrument.

The vibration wave output instrument includes a base, a vibration device, a pressing device and a position mechanism. The vibration device sends vibration waves to a target region. The pressing device drives the vibration device to keep pressing on the target region. The position mechanism is movably installed on the base, and carries both the pressing device and the vibration device to the target region.

Another aspect of the vibration wave output instrument provided in this disclosure includes a base, a movable carrier, a vibration device and a pneumatic cylinder unit. The movable carrier is slidably disposed on the base for moving along an X-axis, a Y-axis or a Z-axis. The vibration device sending vibration waves is fixed on the movable carrier, and moved in accordance with the movable carrier. The pneumatic cylinder unit is fixed on the movable carrier, arranged next to the vibration device, and moved in accordance with the movable carrier. The pneumatic cylinder unit is provided for extending a pneumatic telescopic shaft to keep pressing the vibration device.

The other aspect of the present disclosure is to present a method of using a vibration wave output instrument. The method includes a step of providing a mark on a target region, a step of moving a vibration device to aim at the mark, a step of extending a pneumatic telescopic shaft of a pneumatic cylinder unit by pressurization to push the vibration device, so that a vibration rod of the vibration device is provided to touch against the mark, and a step of outputting vibration waves to the mark by the vibration rod.

As mentioned above, the present disclosure contributes a stable and convenient manner to handle the vibration device, so that the vibration device could stably and precisely aim at a determined tested point of a human body. In addition, enabling the vibration device to keep pressing the skin surface of the human body in one aspect enhances the accuracy that the vibration device points at the tested point of the human body, and in another aspect shortens the distance that the vibration waves move from the skin surface to the interior of the human body so as to improve the precision of the test.

DESCRIPTION OF THE PREFERRED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
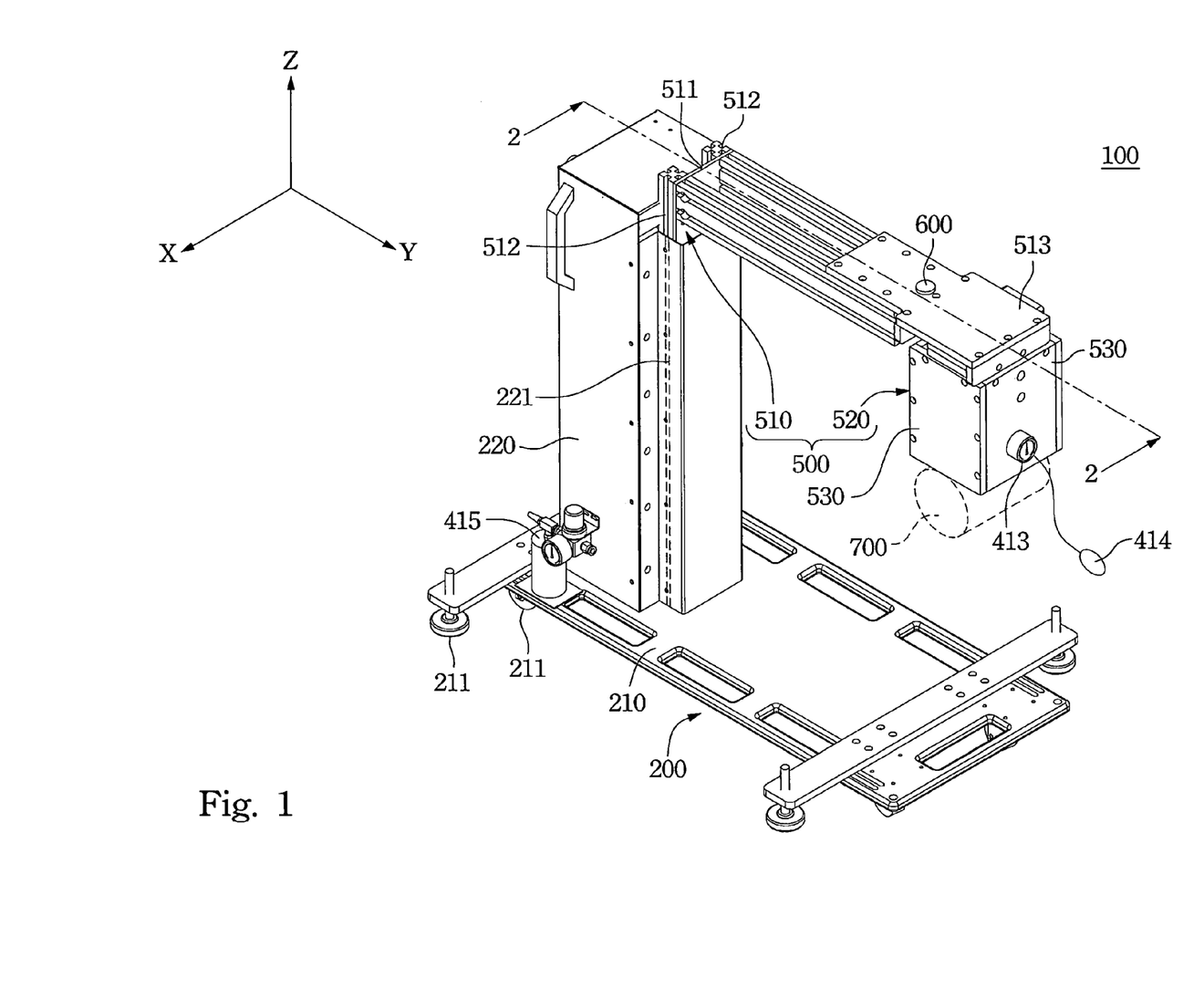
FIG. 1 is a three dimensional view of a vibration wave output instrument in accordance with one embodiment of the present disclosure.
Figure 2:
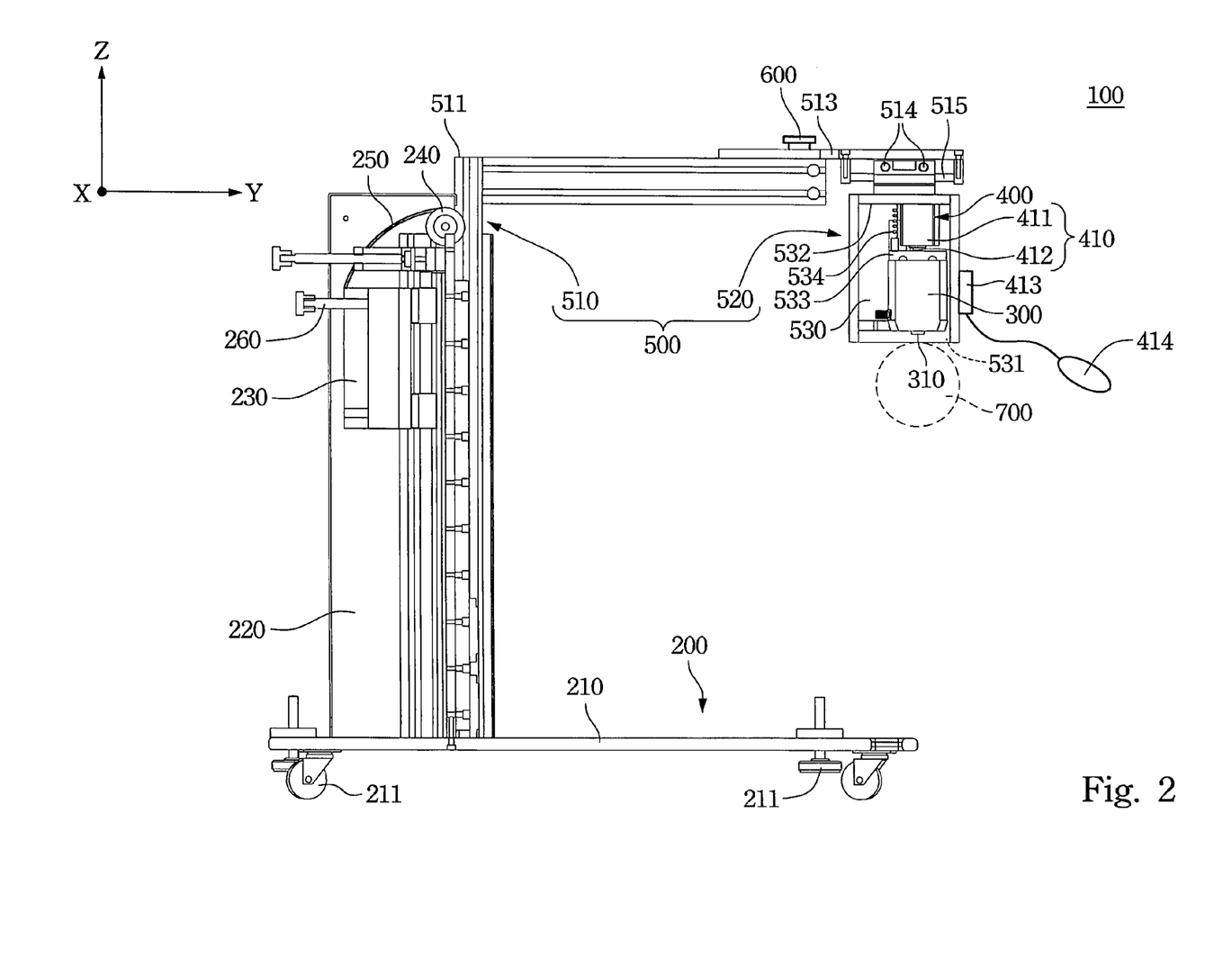
FIG. 2 is a cross-sectional view along a line 2-2 in FIG. 1 of the vibration wave output instrument.

Refer to FIG. 1 and FIG. 2 in which FIG. 1 is a three dimensional view of a vibration wave output instrument in accordance with one embodiment of the present disclosure, and FIG. 2 is a cross-sectional view along a line 2-2 in FIG. 1 of the vibration wave output instrument.

A vibration wave output instrument 100 provided in the disclosure at least has a base 200, a vibration device 300, a pressing device 400 (also called as a pre-press unit, see FIG. 2) and a position mechanism 500.

The vibration device 300 has a vibration rod 310 provided at one end thereof. When the vibration rod 310 touches or presses against a target region 700, the vibration rod 310 outputs vibration waves with a suitable frequency into the interior of the target region 700.

The pressing device 400 is arranged next to the vibration device 300 in which the pressing device 400 is disposed on the other end of the vibration device 300 opposite to the vibration rod 310. Thus, when the pressing device 400 presses the vibration device 300 to move out, the vibration rod 310 could keep touching, or even pressing tightly against the surface of the target region 700. Therefore, it could make sure that the vibration rod 310 can press against the surface of the target region 700 and substantially send the vibration waves into the interior of the target region 700.

The position mechanism 500, which is a collective noun of some elements combined together, is movably installed on the base 200, and coupled with the pressing device 400 and the vibration device 300. Thus, the position mechanism 500 can carry both the pressing device 400 and the vibration device 300 to a determined position neighboring to the target region 700 by moving along an X-axis, a Y-axis or a Z-axis (see FIG. 1).

Therefore, after the vibration waves are sent into the interior of the target region 700, the vibration waves will be reflected from the interior of the target region 700 (i.e. responsive signals). Thus, an operator is able to measure and figure out the condition of the interior of the target region 700 according to the responsive signals.

In a specific embodiment, the target region 700, for example, can be a limited area on a skin surface of a human body, and the interior of the target region 700, for example, can be a human's skeleton. Thus, the information of human bone mineral density and the health condition of the hip joint can be measured and figured out according to the responsive signals.

One way to get the information of human bone mineral density is to calculate the human bone mineral density based on a resonant frequency of the measured responsive signals, so as to further estimate the quality of the human bone. One way to figure out the health condition of the hip joint is to transform the measured responsive signals, so as to further determine that whether these tested hip joints are loose or not.

The detailed components and their arrangements with regard to the base 200, the vibration device 300, the pressing device 400 and the positioning mechanism 500 will be described as follows.

Refer to FIG. 1 and FIG. 2 again. The base 200 includes a foundation 210 and a stand 220. The foundation 210 has a plurality of support feet 211 such as wheels or skid proof feet, for supporting the foundation 210 to stand stably. The stand 220 is vertically disposed on the foundation 210 for sustaining the vibration device 300, the pressing device 400 and the positioning mechanism 500.

Figure 3:
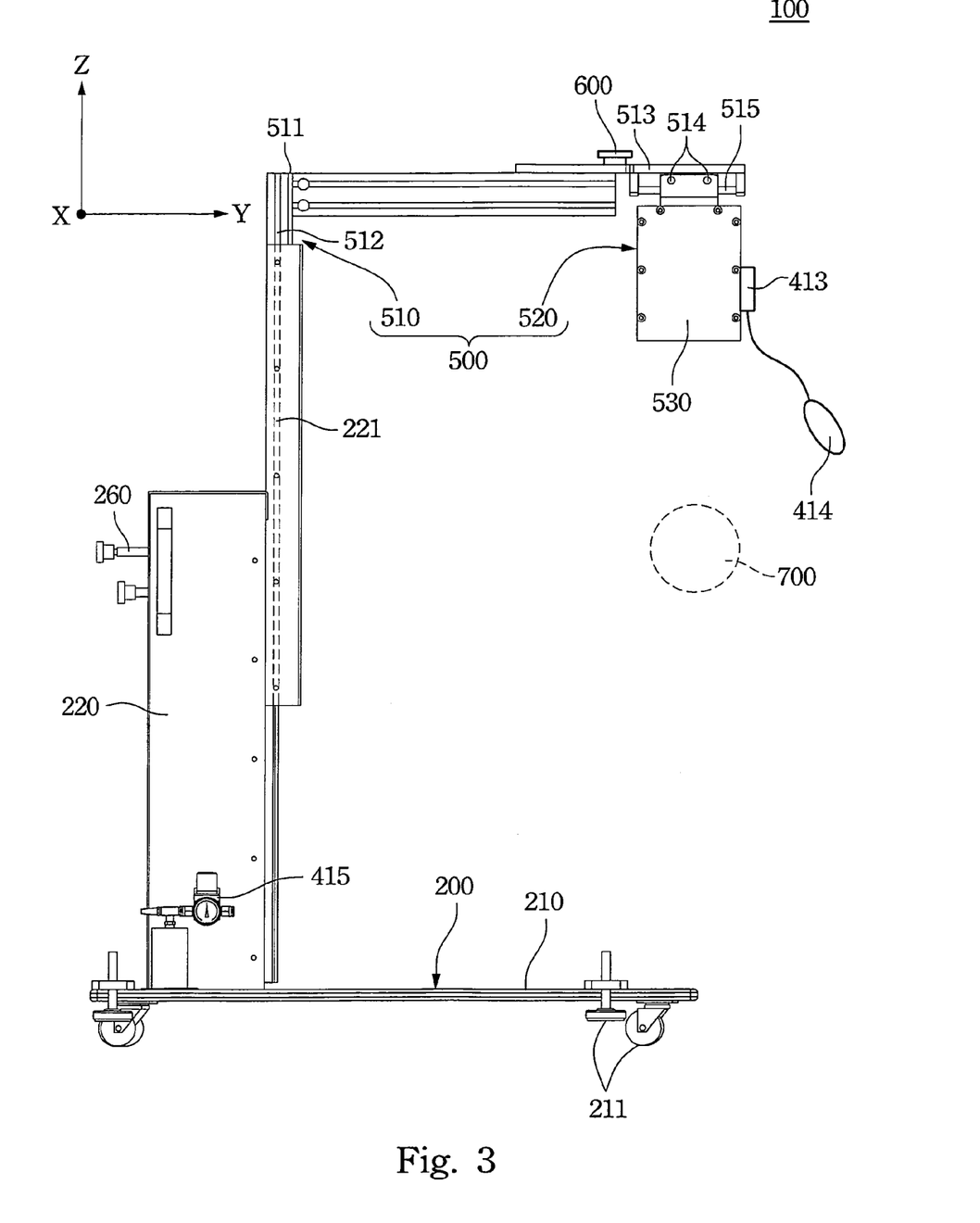
FIG. 3 is one operational schematic view of the vibration wave output instrument in FIG. 1.

Refer to FIG. 1 and FIG. 3 in which FIG. 3 is one operational schematic view of the vibration wave output instrument in FIG. 1. The position mechanism 500 includes a slidable supporting arm 510 and a movable carrier 520. The slidable supporting arm 510 is substantially shown as an "L" shape in the figures, and has a first end 511 and a second end 513 which are opposite with each other. The slidable supporting arm 510 is vertically and slidably disposed on the stand 220 with the first end 511 thereof, and the movable carrier 520 is horizontally and slidably disposed on the second end 513 of the slidable supporting arm 510.

Two opposite sides of the stand 220 have a first Z-axis rail 221, respectively. Two opposite sides of the first end 511 of the slidable supporting arm 510 have a second Z-axis rail 512, respectively. The first Z-axis rails 221 and the second Z-axis rails 512 are respectively corresponding and matching with each other.

Refer to FIG. 1 and FIG. 2 again. The second end 513 of the slidable supporting arm 510 has an X-axis rail 514 and a Y-axis rail 515 which are perpendicular in direction, and are not located on a same plane with each other. Thus, the movable carrier 520 installed on the second end 513 of the slidable supporting arm 510 can be moved with the X-axis rail 514 together along the Y-axis rail 515, or can be moved along the X-axis rail 514.

Therefore, the slidable supporting arm 510 vertically slides along the first Z-axis rails 221 of the stand 220 because the first Z-axis rails 221 and the second Z-axis rails 512 respectively engage with each other. Also, the movable carrier 520 horizontally slides along the X-axis rail or the Y-axis rail on the second end 513 of the slidable supporting arm 510 because the movable carrier 520 engages with the X-axis rail 514 and the Y-axis rail 515.

Figure 4:
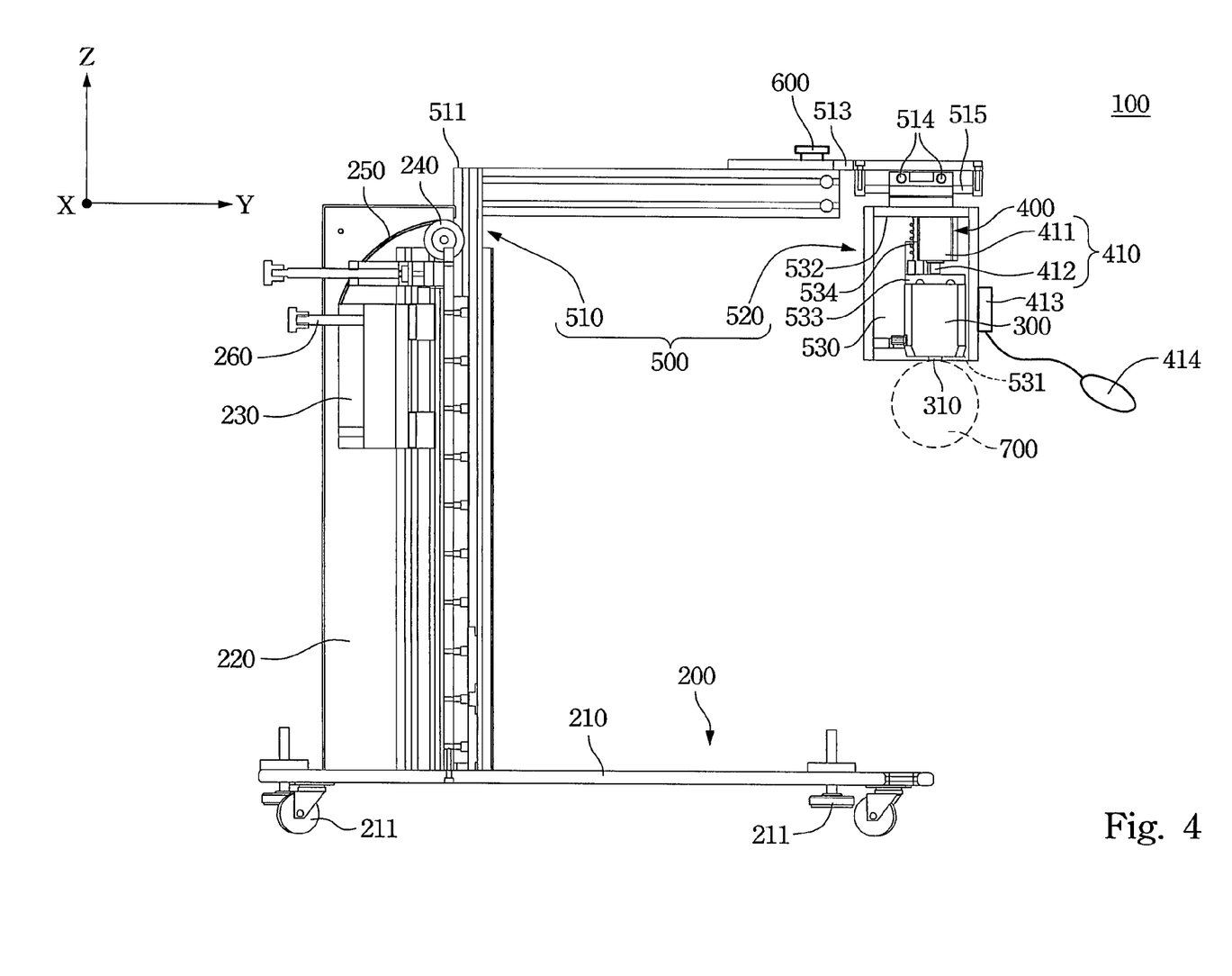
FIG. 4 is one operational schematic view of the vibration wave output instrument in FIG. 1.
Figure 5:
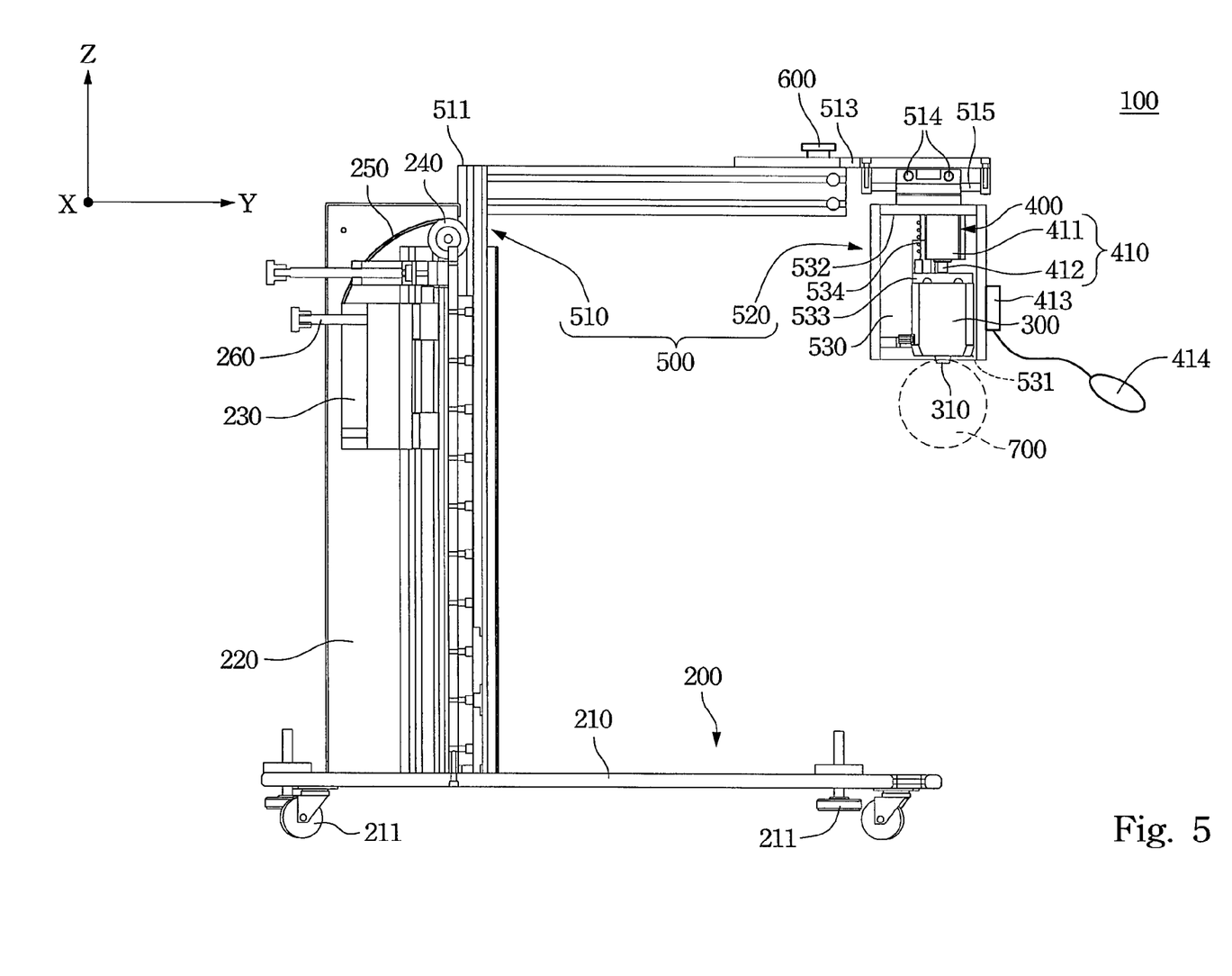
FIG. 5 is another one operational schematic view of the vibration wave output instrument in FIG. 1.

Refer to FIG. 4 and FIG. 5, in which FIG. 4 is one operational schematic view of the vibration wave output instrument in FIG. 1, and FIG. 5 is another operational schematic view of the vibration wave output instrument in FIG. 1.

In this embodiment, the pressing device 400 of the disclosure can be exampled as a pneumatic cylinder unit 410. The pneumatic cylinder unit 410 includes a cylinder body 411, a pneumatic telescopic shaft 412, and an inflatable unit 414. The pneumatic telescopic shaft 412 is extendably disposed in the cylinder body 411 for extending outwards from an end of the cylinder body 411 or drawing back into the cylinder body 411. The inflatable unit 414 is pneumatically communicated with the cylinder body 411 for pressurizing to the cylinder body 411 with air pressure. Hence, when the inflatable unit 414 pressurizes to the cylinder body 411 with air pressure, the pneumatic telescopic shaft 412 extends outwards from the end of the cylinder body 411 to keep pressing the neighboring vibration device 300 to move out.

Therefore, the vibration rod 310 can be ensured to touch or even press against the target region 700, the vibration waves outputted from the vibration rod 310 can be ensured to substantially send into the interior of the target region 700. Meanwhile, the vibration rod 310 will not be easy to separate from the surface of the target region 700 when the human body shakes incidentally.

Also, a barometer 413 can be optionally provided for the pneumatic cylinder unit 410 to show a pressure value representing the degree that the cylinder body 411 has already been pressurized, so that an operator can realize whether the air pressure for the cylinder body 411 is enough by reading the pressure value from the barometer 413. The pressure value read from the barometer 413 also tells information of the force that the pneumatic telescopic shaft 412 has kept pressing the vibration device 300.

It needs to be noted, the pressing device 400 of the disclosure will not be limited to the mentioned pneumatic cylinder unit 410 only, a pre-pressing element (e.g. spring or reed) which exerts a strength on the vibration device 300 and forces the vibration device 300 to move out should be another example of the pressing device 400 other than the mentioned pneumatic cylinder unit 410. Also, the inflatable unit 414 shown in the figures for illustration is only one of the examples. Another one example to press the vibration device 300 can be exampled as a spring set driven by a computerized motor in a total electronic system.

Refer to FIG. 1 and FIG. 4 again. The base 200 is also optionally equipped with an air tank 415. The air tank 415 is pneumatically communicated with the cylinder body 411 and the inflatable unit 414 via connection tubes (the connection tubes are omitted in the figures) to be a buffering space for the cylinder body 411. Thus, when the inflatable unit 414 pressurizes to the cylinder body 411 with air pressure, air would flow into the cylinder body 411 from the air tank 415 to extend the pneumatic telescopic shaft 412 for pressing the vibration device 300 (see FIG. 4, FIG. 5) until the air tank 415 is fully filled. Thus, it allows operators to precisely control the pneumatic telescopic shaft 412 to extend so as to protect the vibration device 300 or the target region 700 from being damaged if the pneumatic telescopic shaft 412 manipulated by the inflatable unit 414 extends too much.

In practice, the movable carrier 520, for example, can be a container 530 (See FIG. 2). The container 530 contains and fixes both the pressing device 400 and the vibration device 300 therein. The container 530 at least has an opening 531, an inner wall 532, a movable board 533 and an elastic element 534. The opening 531 is located at the bottom of the container 530, and normally faces towards the target region 700. The inner wall 532 is in the container 530 for coupling with the pressing device 400 in still.

The movable board 533 is linearly and movably disposed in the container 530, and arranged between the pneumatic cylinder unit 410 and the vibration device 300. The movable board 533 has two opposite surfaces in which one of the surfaces thereof couples to the vibration device 300, and the other surfaces faces the pneumatic telescopic shaft 412 in order to be pressed by the pneumatic telescopic shaft 412.

The elastic element 534 (e.g. spring) has two opposite ends in which one of the opposite ends physically couples with the movable board 533, and the other one of the opposite ends physically couples with a fixed element. In this specification, the so-called fixed element can be an element such as the inner wall 532 (see FIG. 4) staying in a fixed condition while the movable board 533 is in a traveling condition.

Therefore, when the pneumatic cylinder unit 410 is pressurized to extend the pneumatic telescopic shaft 412, the pneumatic telescopic shaft 412 keeps pressing the movable board 533, and then driving the vibration device 300 to move towards the opening 531, and also making the elastic element 534 deformed. Finally, the vibration rod 310 of the vibration device 300 is moved outwards from the opening 531. (See FIG. 5) On the other hand, when the pneumatic cylinder unit 410 is depressurized to draw the pneumatic telescopic shaft 412 back, the elastic element 534 restores to pull the movable board 533 and the vibration device 300 back for the next operation. (See FIG. 2)

In the mentioned embodiment, a power-off device 600 can be further optionally provided on the vibration wave output instrument 100 in order to rapidly cutting off the power in an emergency situation. The power-off device 600 is electrically connected with the pressing device 400 and the vibration device 300, and for example, can be installed on the slidable supporting arm 510 (as shown in the figures), the movable carrier 520 (not shown) or a couple of handling devices respectively grabbed by a tested person or the operators (not shown).

As the power-off device 600 is activated, power for the pressing device 400 and the vibration device 300 is instantly cut off. Therefore, the vibration device 300 stops outputting vibration waves, and the pressing device 400 stops pressing the vibration device 300. For example, the pneumatic cylinder unit 410 immediately exhausts the air in the cylinder body 411 and draws the pneumatic telescopic shaft 412 back to the cylinder body 411.

Thus, the power-off device 600 provided in this embodiment reduces a risk that jeopardizes the target region 700 if the pressing device 400 and the vibration device 300 are operated improperly.

Furthermore, the stand 220 in this embodiment also optionally includes a counterweight 230, a pulley 240, a connection unit 250 and a fixing pin 260. The counterweight 230 is movably arranged in the stand 220. The pulley 240 is pivotally disposed on the stand 220. The connection unit 250 such as a rope or a chain is engaged with the pulley, and one end of the connection unit 250 couples with the slidable supporting arm 510 and the other end of the connection unit 250 couples with the counterweight 230.

Therefore, since a strength that the slidable supporting arm 510 been weighed and a friction occurred between the first Z-axis rail 221 and the second Z-axis rail 512 are equal to a strength that the counterweight 230 been weighed, thus, when an operator pulls the slidable supporting arm 510 down to a height of a position, the slidable supporting arm can be fixed to the position because the strengths are balanced. Finally, the fixing pin plugs on both the stand 220 and the counterweight 230 for fixing the counterweight 230 and remaining the position of the slidable supporting arm 510.

In contrary, when an operator lifts the slidable supporting arm 510 up to another height of a position, since the friction between the first Z-axis rail 221 and the second Z-axis rail 512 has been overcome by the operator, the counterweight 230 is heavy enough to provide strength to lift up the slidable supporting arm 510 by the connection unit 250, so as to facilitate the operator to lift (See FIG. 3).

Figure 6:
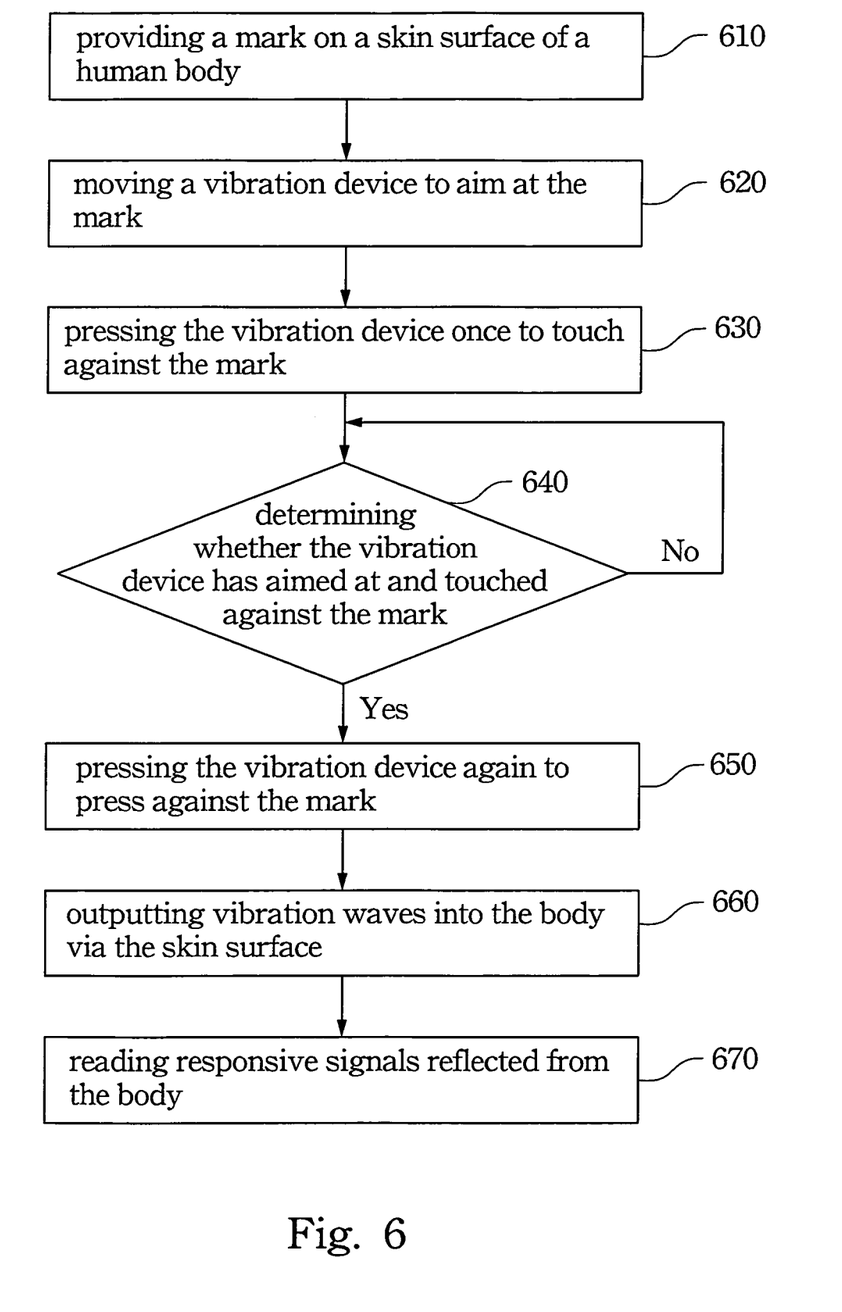
FIG. 6 is a flow chart illustrating a method of using a vibration wave output instrument in accordance with one embodiment of the present disclosure.

Refer to FIG. 2 and FIG. 6 in which FIG. 6 is a flow chart illustrating a method of using a vibration wave output instrument in accordance with one embodiment of the present disclosure. In the followings, the method of using the vibration wave output instrument 100 in accordance with the embodiment will be described below. To be noted, the working mode for those elements mentioned above in the specification above can be performed in a manual way or a machinery (i.e. automatic) way.

Step 610: providing a mark on a skin surface of a body.

In this step, the target region 700 can be a part of skin surfaces on a human body (e.g. a leg), and the mark needs to be made on a predetermined tested position of the skin surface of the human body.

In a manual way, the mark can be marked by an operator, otherwise, in a machinery (i.e. automatic) way, the mark can be practiced as an optically readable mark.

Step 620: moving the vibration device 300 to aim at the mark thereof (See FIG. 3 and FIG. 4).

In a manual way to process this step, the movable carrier 520 can be moved along an X-axis, a Y-axis or a Z-axis by operating the position mechanism 500 by the operator, thus, the vibration device 300 can be moved above the mark thereof and aiming at it.

However, in a machinery (i.e. automatic) way to process this step, the vibration device 300 can be brought to move onto and aim at the mark thereof by a coordinate guiding technology of the electronic system.

Step 630: pressing the vibration device 300 once to touch against the mark thereof (See FIG. 4).

In this step, when the movable carrier 520 is moved above the mark, even touches the skin surface of the target region 700, the operator manually pressurizes the pneumatic cylinder unit 410 by the inflatable unit 414, thus, the pneumatic cylinder unit 410 extends the pneumatic telescopic shaft 412, and then the pneumatic telescopic shaft 412 presses the vibration device 300 to move out so that the vibration rod 310 of the vibration device 300 exactly points to and slightly pressing (i.e. touching) against the mark thereof.

On the other hand, when this step is processed in a machinery (i.e. automatic) way, the electronic system could pressurize the pneumatic cylinder unit 410, and then stop doing so until the vibration rod 310 of the vibration device 300 has exactly pointed to and slightly pressed against the mark thereof.

Step 640: determining whether the vibration device 300 has aimed at and touched against the mark thereof.

In this step, the operator may check whether the vibration device 300 has aimed at and touched against the mark by a manual and machinery way, if yes, process Step 650, otherwise, back to Step 640.

Step 650: pressing the vibration device 300 again to press against the mark thereof (See FIG. 5).

In this step, the operator manually pressurizes the pneumatic cylinder unit 410 again, thus, the pneumatic cylinder unit 410 increasingly extends the pneumatic telescopic shaft 412 to keep pressing the vibration device 300, and the vibration rod 310 of the vibration device 300 will push the vibration device 300 progressively, so that the vibration rod 310 of the vibration device 300 is kept pressing against the mark thereof and a depression of the skin surface of the mark is therefore formed.

On the other hand, when this step is processed in a machinery (i.e. automatic) way, the electronic system could pressurize the pneumatic cylinder unit 410 again to output the air pressure to the pneumatic cylinder unit 410 step by step according to computing programs. In a specific embodiment, the inflatable unit 414 pressurizes the pneumatic cylinder unit 410 about 0.5 kg to 1 kg.

Step 660: outputting vibration waves into the body via the skin surface thereof. (See FIG. 5)

In this step, the vibration device 300 can be activated by a manual way or machinery (i.e. automatic) way, so that the vibration rod 310 outputs vibration waves with the suitable frequency into the human body via the skin surface of the target region 700.

Step 670: reading responsive signals reflected from the body.

In this step, the operator or the electronic system reads the responsive signals reflected from the body by an ultrasonic detector, so as the information of human bone mineral density and the health condition of the hip joint can be measured and figured out according to the responsive signals.

To sum up, the vibration wave output instrument and the method of using the same in the present disclosure contribute a stable and convenient manner to handle, so that the vibration device could stably and precisely aim at a determined tested point of a human body.

In addition, enabling the vibration device to keep pressing the skin surface of the human body in one aspect enhances the accuracy that the vibration device points at the tested point of the human body, and in another aspect shortens the distance that the vibration waves move from the skin surface to the interior of the human body so as to improve the precision of the test.

The reader's attention is directed to all papers and documents which are filed concurrently with his specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A vibration wave output instrument, comprising:
    a base;
    a vibration device for sending vibration waves to a target region;
    a pneumatic cylinder unit for driving the vibration device to press on the target region; and
    a position mechanism movably installed on the base, for carrying both the pneumatic cylinder unit and the vibration device to the target region, the position mechanism comprising a movable carrier, and the movable carrier includes
        a container containing both the pneumatic cylinder unit and the vibration device therein, the container having an opening, wherein when the vibration device is pressed by the pneumatic cylinder unit, the vibration device extends outwards from the opening to the target region,
        a board linearly movably disposed in the container and arranged between the pneumatic cylinder unit and the vibration device, wherein one surface of the board couples to the vibration device, and another surface of the board is pressed by the pneumatic cylinder unit, and
        an elastic element disposed in the container, having two opposite ends respectively coupling with the board and the container.

2. The vibration wave output instrument according to claim 1, wherein the base comprises:
    a foundation; and
    a stand vertically disposed on the foundation, and having a first Z-axis rail.

3. The vibration wave output instrument according to claim 2, wherein the position mechanism comprises:
    a slidable supporting arm having a first end and a second end thereof opposite with each other, and vertically and slidably disposed on the stand with the first end thereof.

4. The vibration wave output instrument according to claim 3, wherein the first end of the slidable supporting arm has a second Z-axis rail engaging with the first Z-axis rail of the stand, and the second end of the slidable supporting arm has an X-axis rail and a Y-axis rail which are not coplanar.

5. The vibration wave output instrument according to claim 4, wherein the movable carrier is horizontally and slidably disposed on the second end of the slidable supporting arm for moving along the X-axis rail or the Y-axis rail.

6. The vibration wave output instrument according to claim 5, wherein the pneumatic cylinder unit comprises:
    a cylinder body;
    an inflatable unit pneumatically communicating with the cylinder body for pressurizing the cylinder body; and
    a pneumatic telescopic shaft extendably disposed on an end of the cylinder body,
    wherein when the inflatable unit pressurizes the cylinder body, the pneumatic telescopic shaft is extended outwards from the cylinder body.

7. The vibration wave output instrument according to claim 6, wherein the base further comprises:
    an air tank pneumatically communicating with both the cylinder body and the inflatable unit for providing a buffering space.

8. The vibration wave output instrument according to claim 6, further comprising a power-off device electrically connected with the pneumatic cylinder unit and the vibration device for cutting off the power to the pneumatic cylinder unit and the vibration device.

9. The vibration wave output instrument according to claim 5, wherein the pneumatic cylinder unit is a pre-pressing unit having two opposite ends respectively coupled with the container and the vibration device, and the pre-pressing unit is for forcing the vibration device to move towards the opening.

10. The vibration wave output instrument according to claim 1, wherein the target region is a part of skin surface.

11. The vibration wave output instrument according to claim 3, wherein the stand comprises:
- a counterweight;
- a pulley pivotally disposed on the stand;
- a connection unit engaged with the pulley, and having two opposite ends respectively coupled with the counterweight and the slidable supporting arm; and
- a fixing pin pluggably disposed on the stand for fixing the counterweight to remain the position of the slidable supporting arm.

* * * * *